(12) United States Patent
Moshfeghi et al.

(10) Patent No.: US 6,216,104 B1
(45) Date of Patent: *Apr. 10, 2001

(54) COMPUTER-BASED PATIENT RECORD AND MESSAGE DELIVERY SYSTEM

(75) Inventors: Mehran Moshfeghi, Sunnyvale; Robert A. Glicksman, San Jose, both of CA (US)

(73) Assignee: Philips Electronics North America Corporation, New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/027,125
(22) Filed: Feb. 20, 1998
(51) Int. Cl.[7] ........................................... G10L 5/00
(52) U.S. Cl. ............................... 704/260; 704/270
(58) Field of Search ................... 704/258, 260, 704/270, 275, 200, 272, 273

(56) References Cited

U.S. PATENT DOCUMENTS

| | | | |
|---|---|---|---|
| 5,243,643 | * | 9/1993 | Sattar et al. ............................ 379/88 |
| 5,333,266 | * | 7/1994 | Boaz et al. ....................... 395/200.36 |
| 5,493,692 | * | 2/1996 | Theimer et al. . |
| 5,633,910 | * | 5/1997 | Cohen ..................................... 379/38 |
| 5,706,507 | * | 1/1998 | Schloss ................................ 707/104 |
| 5,721,827 | * | 2/1998 | Logan et al. ..................... 395/200.47 |
| 5,732,216 | * | 3/1998 | Logan et al. ..................... 395/200.33 |
| 5,742,668 | * | 4/1998 | Pepe et al. ............................. 455/415 |
| 5,761,201 | * | 6/1998 | Vaudreuil ............................... 370/392 |
| 5,812,865 | * | 9/1998 | Theimer et al. ................. 395/200.58 |
| 5,845,255 | * | 12/1998 | Mayaud ................................. 705/3.2 |
| 5,884,266 | * | 3/1999 | Dvorak .................................. 704/275 |

FOREIGN PATENT DOCUMENTS

| 2134132 | | 7/1995 | (CA) | ............................. H04M/11/06 |
|---|---|---|---|---|
| WO 99/42932 | * | 8/1999 | (WO) | ................................ G06F/17/30 |

OTHER PUBLICATIONS

MIT Media Laboratory. Arons, "Hyperspeech: Navigating in a speech–only Hypermedia"., PP 133–146. Dec, 1991.*

Speech Communication. Taylor et al., "SSML: a speech synthesis markup language" vol. 21, p. 123–33, Feb. 1997.*

"SSML: A Speech Synthesis Markup Language", by P. Taylor et al., Speech Communication 21, 1997, pp. 123–133.

* cited by examiner

*Primary Examiner*—Richemond Dorvil
(74) *Attorney, Agent, or Firm*—John F. Vodopia

(57) ABSTRACT

A Computer-based Patient Record (CPR) system includes user equipment devices which are configured for speech synthesis in response to speech markup language text and which are connected via a network to a middle tier of a server system. The CPR system further includes a message delivery facility for delivery of textual messages to any of pager, electronic mail, or voice mail (after text-to-speech synthesis) message delivery vehicles. The server system accesses a user specific data store containing speech synthesis profiles which include prosodic information of the voices and speech of users, and message delivery profiles which specify which of the aforementioned message delivery vehicles are to be used and in what order. The stored speech synthesis information associated with an originator of a message and the stored message delivery information associated with the recipient of message are provided by the server to user equipment or a reminder generator to produce speech markup files containing information needed to synthesize the vocal and speech characteristics of the originator accompanied by delivery instructions reflecting the message delivery preferences of the recipient.

17 Claims, 1 Drawing Sheet

COMPUTER-BASED PATIENT RECORD AND MESSAGE DELIVERY SYSTEM

BACKGROUND OF THE INVENTION

1. Field of the Invention

The present invention relates generally to a computer system for enabling access of records in electronic form via a network, such as an intranet, which includes a facility for delivery of messages. In its particular aspects, the present invention relates to such a system in which audible messages are generated by text-to-speech synthesis. The invention is particularly useful in the medical domain in conjunction with Computer-based Patient Record (CPR) systems and in the provision of alerts to physicians and other health care professionals.

2. Description of the Related Art

CPR systems maintain multimedia patient records of one or more health care institutions such as histories, reports, charts, and images in electronic digital form in a server system so that authorized users may access the records remotely employing user equipment, such as desktop or portable computing devices, coupled to the server system via wired and/or wireless network paths.

Speech interfaces for computer systems can employ speech recognition for command and control, thereby providing for hands-free navigation by the user. Also, useful information can be optimally arranged on screen and the user can remain focussed thereon by eliminating distracting and space consuming Graphical User Interface (GUI) control objects such as buttons, hot spots and/or menus that are typically used with a mouse or other pointing device. Speech recognition for dictation can enable health care personnel to enter reports when their hands are busy or where touching a keyboard would be a hygiene risk.

Text-to-speech synthesis can provide background notification of events and status changes, such as printer activity, by speech synthesized messages thereby avoiding visual distraction of the user. The use of synthesized speech for audible messages also minimizes storage requirements for the messages.

A Java® Speech Application Programming Interface (API) is substantially available to support speech synthesis, command-and-control recognizers and dictation systems. The Java® Speech API includes a Java® Speech Markup Language (JSML) for speech synthesis and a Java® Speech Grammar Format (JSGF) for speech recognizers. JSGF provides rule-based grammar indicating possible alternative commands, actions, objects, and their relative probabilities. JSML supports explicit specifications for delimited words and phrases such as structure (paragraph and sentence), special handling of dates and times, breaks, and prosodic information (speaking rate, volume, baseline pitch, pitch range).

In hospital environments, health care personnel are not always at their user equipment devices and there is a need to issue alerts and reminders via the CPR system which can be received via a variety of message delivery vehicles, such as voice mail, pager, and electronic mail. Further, there is a need that such alerts and reminders when delivered as audible messages have appropriate clarity, structure, and prosodic characteristics, so they are easily understandable and receive attention appropriate to the nature of the information conveyed.

SUMMARY OF THE INVENTION

It is an object of the present invention to provide a message delivery facility in a computer network system which includes speech synthesis of text specified in a speech markup language, such as JSML.

It is a further object of the present invention that the text specified in speech markup language include speaker profile information so that the message may be personalized with prosodic characteristics of the voice of a predetermined person, for example the originator of the message, in order to invoke appropriate attention by the recipient.

It is yet another object of the present invention that the computer system provide for delivery of messages in accordance with a message delivery profile of the recipient indicating which message delivery vehicles should be used and in what order.

Briefly, these and other objects are achieved by providing a computer system, including a server system and user equipment devices coupled thereto by a network, wherein the server system has access to a storage system containing user specific information including speech synthesis profiles of users of the system, each profile of a user including prosodic information for synthesizing vocal characteristics of the user, such as baseline pitch and pitch range, and including message delivery profiles of users indicating which of a plurality of possible message delivery vehicles are to be used, and in what order. The computer system has the capability of generating messages in the form of speech markup language text which includes prosodic information of a predetermined person associated with the message, usually the originator, to be initiated and supplied to a message delivery system for delivering the message to the recipient in accordance with the recipient's stored message delivery profile.

The message delivery system includes a speech synthesizer for receiving the speech markup language text and synthesizing therefrom an audible message, which is similar in vocal characteristics to the predetermined person, and also appears clear and natural due to the use of delimiters in the markup language text specifying emphasis or volume, speaking rate, and items to be said as dates and times. The message delivery system includes as one of the message delivery vehicles, a voice mail facility which receives synthesized speech from the speech synthesizer. Other message delivery vehicles of the message delivery system include a pager system, and an electronic mail system.

Other objects, features and advantages of the present invention will become apparent upon perusal of the following detailed description when taken in conjunction with the appended drawing, wherein:

DETAILED DESCRIPTION OF THE PREFERRED EMBODIMENTS

Figure 1:
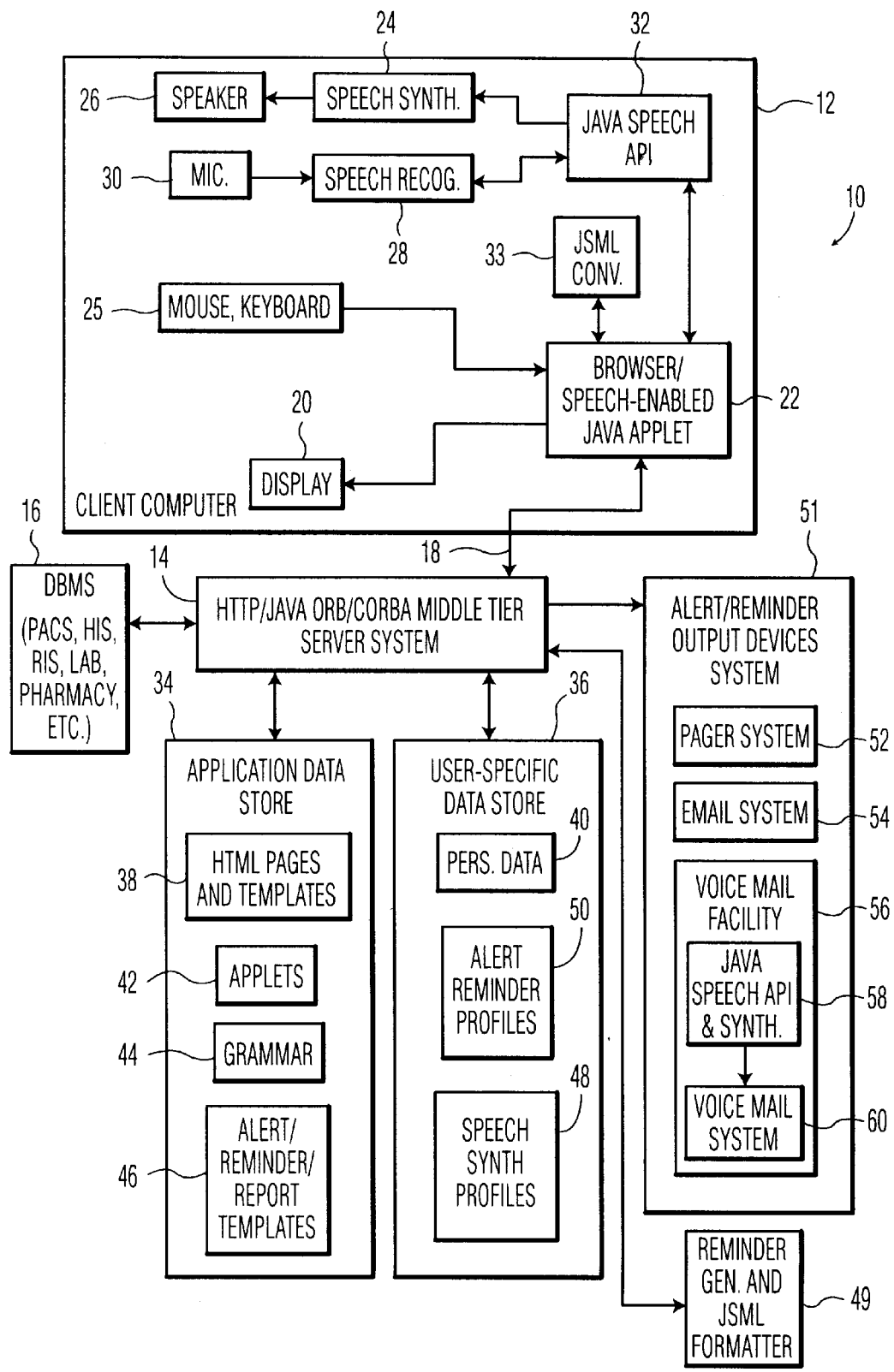
FIG. 1 is a schematic diagram of a speech enabled CPR system accordance with the present invention which is capable of generating alerts, reminders, and reports in the form of a speech markup language.

Referring to FIG. 1 of the drawing, there is shown a computer system 10 for delivery of Computer-based Patient Records (CPRs) to users at user equipment devices, or client computers 12, 12' and 12" of which computer 12 is illustrated in detail, from a server system generally comprising servers 14 and 16, via network paths such as 18, 18' and 18", respectively.

Server 14 may be one or a plurality of servers configured to together perform the functions of a Hypertext Transfer Protocol (HTTP) server and also a Common Object Request Broker Architecture (CORBA) server, using Internet-Inter-Orb Protocol (IIOP), which act as a middle tier between the user equipment devices or client computers and the back end server 16 which is a Database Management System in communication with the various information systems of the health care institution(s), including Picture Archiving and Communications System (PACS), Hospital Information System (HIS), Radiology Information System (RIS), laboratory computing system, and pharmacy computing system, in order to supply requested patient information objects to middle tier server 14. This middle tier server provides services to HTTP clients and CORBA clients via an intranet accessible via network paths 18. CPR information may be presented on the display 20 of exemplary user equipment employing web-based tools such as Hyper Text Mark-up Language (HTML) pages and Java® (a trademark of Sun Microsystems, Inc.) applets that are downloaded to the user equipment by server 14 also acting as a Java® Object Request Broker (ORB), which downloaded applets and run thereon inside a web browser. The browser/ Java® applet combination is represented by the element 22. User equipments 12, 12' and 12" and the applets downloaded thereto, are preferably speech-enabled. Thus, exemplary user equipment 12 includes a speech synthesizer 24 which feeds a speaker 26, and a speech recognition engine or recognizer 28 which is fed by a microphone 30. However, the usual input devices, such as mouse and keyboard 25 should also be provided. As is usual, speech synthesizer 24 and speech recognition engine 28 may be realized by software. Recognizer 28, which is preferably used both for command and control purposes and for dictation purposes, includes a lexicon and may be further constrained by a context appropriate to the subject or specialty of the user. For purposes of illustration, synthesizer 24 and recognizer 28 are shown separately coupled to applet/browser combination 22 via Java® Speech Application Programming Interface (API) 32. The connection 34 between recognition engine 28 and the Java® Speech API is shown as bidirectional, because grammar in Java® Speech Grammar Format (JSGF) is sent to the recognizer 28 for command and control recognition purposes. Preferably only the subset thereof applicable to the current screen display is sent from the applet to the recognizer to improve the recognition accuracy.

In addition to command and control necessary to access patient records, users input text which may be medical reports of particular patients or messages, such as alerts, for particular recipients. This text may be inputted and placed into appropriate fields of an associated downloaded template by the user via the microphone 30 and speech recognition engine 28, via mouse and keyboard 25, or a combination thereof.

Exemplary user equipment 12 also contains a Java® Speech Markup Language (JSML) converter 33 which is preferably implemented by software under control of the applet and is shown functionally in bidirectional communication with the browser/applet combination 22. Its purpose is to receive user inputted or application generated text and a template which is associated with the text or in which the text is embedded and to produce a JSML text file therefrom. The template, which has previously been downloaded from server 14, has fields or defined locations in which text is embedded or with which text is associated and respective JSML delimiters are associated in one to one correspondence with respective fields. Consequently, through the use of JSML delimiters, such things as volume or emphasis, speaking rate, pitch change, and whether text should be said as a date or said as a time can be individually specified for the text of each field. In accordance with the invention, the JSML converter 33 has the capability of producing a JSML file in which prosodic information such as the baseline pitch and pitch range (and may include other information such as age and sex of the speaker) which are taken from user specific speech synthesis profile information downloaded to exemplary user equipment 12 by server 14 are specified for the entire JSML file. Thus, the JSML file also contains information which allows a speech synthesizer, such as 24, to synthesize speech having the vocal characteristics of a predetermined person associated with the text, such as the originator or author thereof. The prosodic characteristics which can be specified to approximate the voice and speech of a predetermined speaker are not necessarily limited to those specifically provided for in JSML as possible delimiters, since JSML may also contain native instructions to a specified speech recognizer.

An application data store 34 and a user specific data store 36 are coupled to or accessible by server 14. Stores 36 may be implemented together in a single storage device or in a combination of such devices. Application data store 34 includes at area 38, Hypertext Markup Language (HTML) pages and templates for server 14 to form HTML pages in accordance with personalization information stored in user specific data store 36 at area 40. This personalization information includes the specialty or title and affiliation of the user, specifications of the user's exemplary equipment 12 including display type or resolution, and the limiting bandwidth in the network path 18 between server 14 and exemplary user equipment 12. After the user logs on to the system at the user equipment and presents his ID and password and requests patient formation or a list of patients, server 14 retrieves the personalization information and uses it to generate HTML pages to be supplied to the user equipment which are appropriate to the user, his relationship to the patient(s), and the capability of his equipment and network connection. The inclusion of such capability information allows the server 14 to limit the use of or number of pixels in graphical objects in the HTML pages where the display is low resolution (or text only) or the limiting bandwidth includes a relatively low baud rate telephone or wireless path which would otherwise produce unacceptably long download times for such objects.

Application data store 34 also contains applets in area 42 and associated speech recognition grammar files in area 44 which are read by server 14 and downloaded to the user equipment when needed. Further, application data store 34 includes alert, reminder and report templates at area 46 and the user specific data store includes speech synthesis profiles at area 48 which are used by JSML converter 33 to produce JSML text files which are personalized to the voice of a predetermined speaker. The reminder templates and speech synthesis profiles are used by a reminder generator and JSML formatter 49. The latter device is configured to maintain a store of scheduled reminders from particular originators to particular recipients at predetermined times, having predetermined text in fields of an associated reminder template. At some time prior to the scheduled delivery time generator and formatter 49 produces a JSML text file therefrom in a similar manner as the JSML converter 33 operates. Then, alert/reminder profile data stored in area 50 of specific data store is accessed by generator and formatter 49 via server 14 to determine which message delivery vehicles are to be used, their characteristics, and in which order they should be tried. Generator and formatter 49 uses this information to produce delivery instructions which are sent along with the JSML text file to alert/reminder output devices system 51 via server 14. Output devices system includes a pager system 52 for delivery of plain text messages to designated pagers carried by users, an electronic mail system 54 which can be accessed by users from a variety of types of wired or wireless communications or computing devices (e.g. Personal Digital Assistants (PDAs), cellular or wireless local loop phones, screen telephones), and a voicemail facility 56. The latter includes a speech synthesizer 58 (including the necessary parts of Java® Speech API) and a conventional voice mail system, which users may access by telephone to hear audible messages. In the case of message delivery to electronic mail system 54, it is expected that the delivery instructions will include whether or not the textual message should include JSML delimiters or whether they should be removed.

In a similar manner, when alerts are composed by a user at user equipment, server 14 will send to the user equipment an alert/reminder profile of the intended recipient so that delivery instructions may be produced by user equipment. The alert with accompanying delivery can be sent from the user equipment to output device system 51 via server 14.

It should now be appreciated that the objects of the present invention are satisfied.

While the present invention has been described in particular detail, it should also be appreciated that numerous modifications are possible within the intended spirit and scope of the invention.

All references cited herein, in particular those to particular computer languages, systems, and standards, are incorporated herein by reference in their entirety and for all purposes to the same extent as if each individual publication or patent or patent application was specifically and individually indicated to be incorporated by reference in its entirety for all purposes.

What is claimed is:

1. A computer system comprising:
   a server system;
   a plurality of user equipment devices coupled to the server system via a network;
   an application data store and user-specific data store accessible to the network and containing user specific information of users of the system, the user specific information comprising (i) user speech synthesis profiles including prosodic information for synthesizing vocal characteristics of the user, and (ii) user message delivery profiles indicating which of a plurality of possible message delivery vehicles are to be used for message delivery to the user;
   means at user equipment for an originating user to initiate production of a message for a recipient user, said message comprising speech markup language text which includes prosodic information from the speech synthesis profile of a determined user downloaded to the user equipment by the server; and
   a message delivery system for delivering the message to the recipient user in accordance with the recepient user's stored message delivery profile.

2. The system as claimed in claim 1, wherein the message delivery system includes a speech synthesizer for receiving the speech markup language text and synthesizing therefrom an audible message, which is similar in vocal characteristics to the determined user.

3. The system as claimed in claim 2, wherein the message delivery system includes as one of said message delivery vehicles, a voice mail facility which receives synthesized speech from said speech synthesizer.

4. The system as claimed in claim 3, wherein the message delivery system includes as another of said message delivery vehicles, a pager system.

5. The system as claimed in claim 4, wherein the message delivery system includes as another of said message delivery vehicles, an electronic mail system.

6. The system of claim 1, wherein said determined user is the originating user.

7. The system of claim 1, wherein said prosodic information includes for each user, baseline pitch, and pitch range.

8. The system of claim 1 wherein the speech markup language comprises JAVA® speech markup language.

9. The system of claim 1 further comprising
   an alert and reminder generator and formatter, and
   wherein the application data store and user-specific data store contains application specific information, the application specific information comprising alert and reminder templates for scheduled alert and reminder messages from originating users to recipient users, and wherein
   the alert and reminder generator and formatter (i) produces scheduled alert or reminder messages for the recipient user from the originating user, said alert or reminder messages comprising speech markup language text which includes prosodic information from the speech synthesis profile of a determined user, and (ii) delivers the produced alert or reminder messages to the recipient user in accordance with the recipient user's stored message delivery profile.

10. A method for message delivery from originating users of a computer system to recipient users of the computer system, the method comprising:
    providing in the computer system an application and a user-specific data store containing user specific information of users of the system, the user specific information comprising (i) user speech synthesis profiles including prosodic information for synthesizing vocal characteristics of the user, and (ii) user message delivery profiles indicating which of a plurality of possible message delivery vehicles are to be used for message delivery to the user, producing a message from an originating user to a recipient user, the message comprising speech markup language text which includes prosodic information from the speech synthesis profile of a determined user which is stored in the application and user-specific data store, and delivering the message to the recipient user in accordance with the recipient user's message delivery profile which is stored in the application and user-specific data store.

11. The method of claim 10 wherein said step of producing a message further comprises:

retrieving a message template comprising fields with delimiters for specifying characteristics guiding subsequent speech synthesis providing message text, and embedding said message text in said message template.

12. The method of claim 10 wherein said message text either is provided by user input, or is provided by application generation, or is predetermined.

13. The method of claim 10 further comprising, after said step of delivering, a step of receiving said message at a user equipment device, at least one user equipment device being provided in the computer system.

14. The method of claim 13 wherein the user equipment device comprises a speech synthesizer, and wherein said step of receiving said message further comprises synthesizing said message into an audible message for said recipient user, whereby the audible message appears clear, natural, and similar in vocal characteristics to the determined user due to synthesis guidance by said speech profile information and by said message template delimiters.

15. The method of claim 10 wherein said prosodic information for a user includes baseline pitch and pitch range.

16. The method of claim 10 wherein said speech markup language is JAVA® speech markup language.

17. The method of claim 10 wherein a server system and at least one user equipment device are provided in the computer, and wherein said step of producing a message further comprises retrieving the speech synthesis profile from the server system to the user equipment device.

* * * * *